(12) United States Patent
Aravena et al.

(10) Patent No.: US 6,244,867 B1
(45) Date of Patent: Jun. 12, 2001

(54) MULTI-PART, MULTI-POSITIONABLE ABUTMENT FOR USE WITH DENTAL IMPLANTS

(75) Inventors: Ines M. Aravena, Camarillo, CA (US); Gerald A. Niznick, Las Vegas, NV (US)

(73) Assignee: Sulzer Dental Inc., Houston, TX (US)

( * ) Notice: Subject to any disclaimer, the term of this patent is extended or adjusted under 35 U.S.C. 154(b) by 0 days.

(21) Appl. No.: 09/198,651

(22) Filed: Nov. 24, 1998

(51) Int. Cl.⁷ ........................................................ A61C 8/00
(52) U.S. Cl. ............................................. 433/172; 433/173
(58) Field of Search ..................................... 433/172, 173

(56) References Cited

U.S. PATENT DOCUMENTS

| | | | |
|---|---|---|---|
| 5,069,622 | * | 12/1991 | Rangert et al. ...................... 433/173 |
| 5,281,140 | * | 1/1994 | Niznick ................................. 433/172 |
| 5,449,291 | * | 9/1995 | Lueschen et al. .................... 433/172 |
| 5,564,921 | * | 10/1996 | Marlin ................................... 433/172 |
| 5,577,912 | * | 11/1996 | Prins ..................................... 433/172 |
| 5,662,473 | * | 9/1997 | Rassoli et al. ........................ 433/172 |
| 5,863,200 | * | 1/1999 | Hamada et al. ...................... 433/173 |
| 5,882,200 | * | 3/1999 | Sutter et al. .......................... 433/173 |

* cited by examiner

Primary Examiner—John J. Wilson
(74) Attorney, Agent, or Firm—Patrick F. Bright

(57) ABSTRACT

A multi-part abutment adapted for use with dental implants such as cylindrical-shaped endosseous dental implants having an internal opening or passage with an internal, non-circular shape at the top, either internally or externally, includes part one that engages the opening or passage in, or projection at the top, of the implant at the distal end of part one, and fits into abutment part two, at the top end of part one. Part two has at its distal end a multi-sided cavity that interdigitates with a multi-sided periphery or other connector on part one so that part two can be placed in a plurality of positions over part one. At the top end of part two is a prosthesis-engaging or prosthesis-forming projection which may be at an angle to the longitudinal axis of the implant, or lie on the longitudinal axis of the implant. Internal passages inside the two abutment parts are colinear when joined to one another in their intended configuration, permitting the use of a single fastener to join the two abutment parts to one another and to the dental implant, with part two covering part one and forming a sealed margin with the top of the implant.

11 Claims, 4 Drawing Sheets

MULTI-PART, MULTI-POSITIONABLE ABUTMENT FOR USE WITH DENTAL IMPLANTS

This invention relates to multi-part abutments adapted for use with dental implants, particularly endosseous dental implants, and, more particularly, cylindrical-shaped endosseous dental implants. Such abutments have multiple parts, namely a first part called a connector, and a second part that may, for example, be an angled abutment body or a straight abutment body that can be placed in any one of a plurality of desired positions. In preferred embodiments, these multiple parts are secured to a dental implant by a single fastener that joins the multiple parts of the abutment to one another, and to the implant. When the multi-part abutment is seated atop a dental implant, the body covers the connector, and forms a single, preferably sealed, external margin with the top surface of the implant.

The multi-part abutment of this invention comprises part one, denoted a connector, having a projection of a shape and size, at its distal end, that is adapted to fit into an opening or passage at the proximal end of a dental implant. Alternatively, part one may have a recess of a shape and size, at its distal end, that is adapted to fit over a projection, such as a multi-sided projection, at the proximal end of a dental implant.

Part one includes a multi-featured, preferably a multi-sided surface, on its external wall. This surface has a size and shape adapted to engage a preferably frictionally, features of complementary size and shape at or near the bottom end of abutment part two. In preferred embodiments, a multisided surface has, for example, six to twelve faces or sides to permit connection to abutment part two, denoted a body, which has a complementary cavity or opening with, for example, from six to twelve faces or sides. These complementary configurations permit part two to be placed in any one of a plurality, e.g. six to twelve positions over part one. Alternatively, part one may include connecting features other than a multisided surface that engage complementary connecting features in a cavity or opening in part two, such as spines, grooves or slots and projections, and pins and holes or slots.

Parts one and two also include a passage along their longitudinal axes for receiving a fastener. Such a fastener preferably includes a shaft that passes through the passage in part two, through a similar, colinear passage in part one, and into the passage or opening at the top of the dental implant. There, the fastener is adapted to engage the passage or opening at the top of the implant. Preferably, a threaded portion at the distal end of the fastener engages complementary threads on the interior wall of the passage or opening in the dental implant.

Part two preferably includes, at its distal end, a multi-sided cavity of a size, shape and configuration that interdigitates and connects with the multi-sided surface on the external wall of part one. This distal end of part two has, in such preferred embodiments, a multi-sided cavity with e.g. six to twelve sides or faces to permit part two to interdigitate in any one of a number of positions over part one.

Part two has, at its proximal end, a prosthesis-engaging or prosthesis-forming portion that can be of any desired size or shape, and formed at any angle with respect to the longitudinal axis of the abutment. In some embodiments, this proximal end of part two has a frusto-conical-shaped portion that lies along the longitudinal axes of the two parts, where it forms an angle with respect to the longitudinal axes of the two parts.

In preferred embodiments, part two, like part one, includes a passage along its longitudinal axis for receiving a fastener. This longitudinal passage is of a size, shape and configuration that is substantially similar to the size, shape and configuration of the longitudinal passage in part one so that a single fastener can pass through both passages, joining abutment parts one and two to one another and to a dental implant. Thus, as in part one, the passage is preferably cylindrical in shape, and includes an internal shelf or flange for engaging one end of the single fastener that is adapted to join the two parts to one another, and to a dental implant.

In preferred embodiments, the fastener includes a cylindrical-shaped shaft having a threaded portion at its distal end, and having a flange at its upper end that is of a size and shape adapted to engage the shoulder or flange in the interior passage of abutment part two. Alternatively, the shaft can have, at its distal end, a portion of a size and shape adapted to frictionally engage, or cement into a passage or opening inside the top of a dental implant.

Thus, the abutment of this invention includes a connector, denoted part one, and an abutment body, denoted part two, that fits over part one, and seats, preferably sealingly, atop a dental implant, thus providing a low profile abutment assembly. This two part abutment can be placed in a plurality of positions, as desired, and can be joined to a dental implant with a single fastener, preferably a fixation screw.

In preferred embodiments, the abutment body and connector are friction-fitted to one another. The resulting body/connector assembly is also friction-fitted to the complementary structure of existing dental implants, including dental implants with an external projection and dental implants with an internal, multi-sided passage or other abutment/implant connection structure.

In preferred embodiments, the connector may have, at its distal end, an external taper-lock, multi-sided structure, or an internal multi-sided structure for attachment to an implant. Preferably, the connector includes internal threads to engage a tool that disengages the connector from the implant.

In preferred embodiments, the abutment body has an internal multisided cavity at or near its distal end for connection to a multi-sided external wall projection on the connector (part one). The proximal end of the body includes an access hole for a fixation screw. Internal threads in the passageway through the body portion include internal threads to engage a tool that can disengage the body from the connector.

The outer structure of the body can vary depending upon its intended function or use. An angled body provides an angulation adjustment to the longitudinal axis of an implant. Such a body may be rotated to and placed in a desired orientation using the interdigitating multi-sided connections between the connector and body assembly. Because the connector and the body are separate, the body can be cast to gold with no connector attached, thus avoiding deformation of the connector during casting. The abutment body can be joined to an implant without the connector, if desired, or with the connector to form a multi-part abutment.

In preferred embodiments, the multi-part abutment of this invention is packaged with an angled, one piece carrier, preferably a plastic carrier. This carrier delivers the connector at a desired angle and orientation to an implant placed in the jawbone of a patient. The distal end of the carrier includes an internal multi-sided cavity to engage the connector. This cavity is at an angle to the axis of the carrier's body to facilitate proper placement of the connector, thus establishing precise indexing and positioning of the connector's lower end on an implant's upper end.

BRIEF DESCRIPTION OF THE DRAWINGS

This invention can better be understood by reference to the drawings, in which.

DESCRIPTION OF THE PREFERRED EMBODIMENTS

Figure 1:
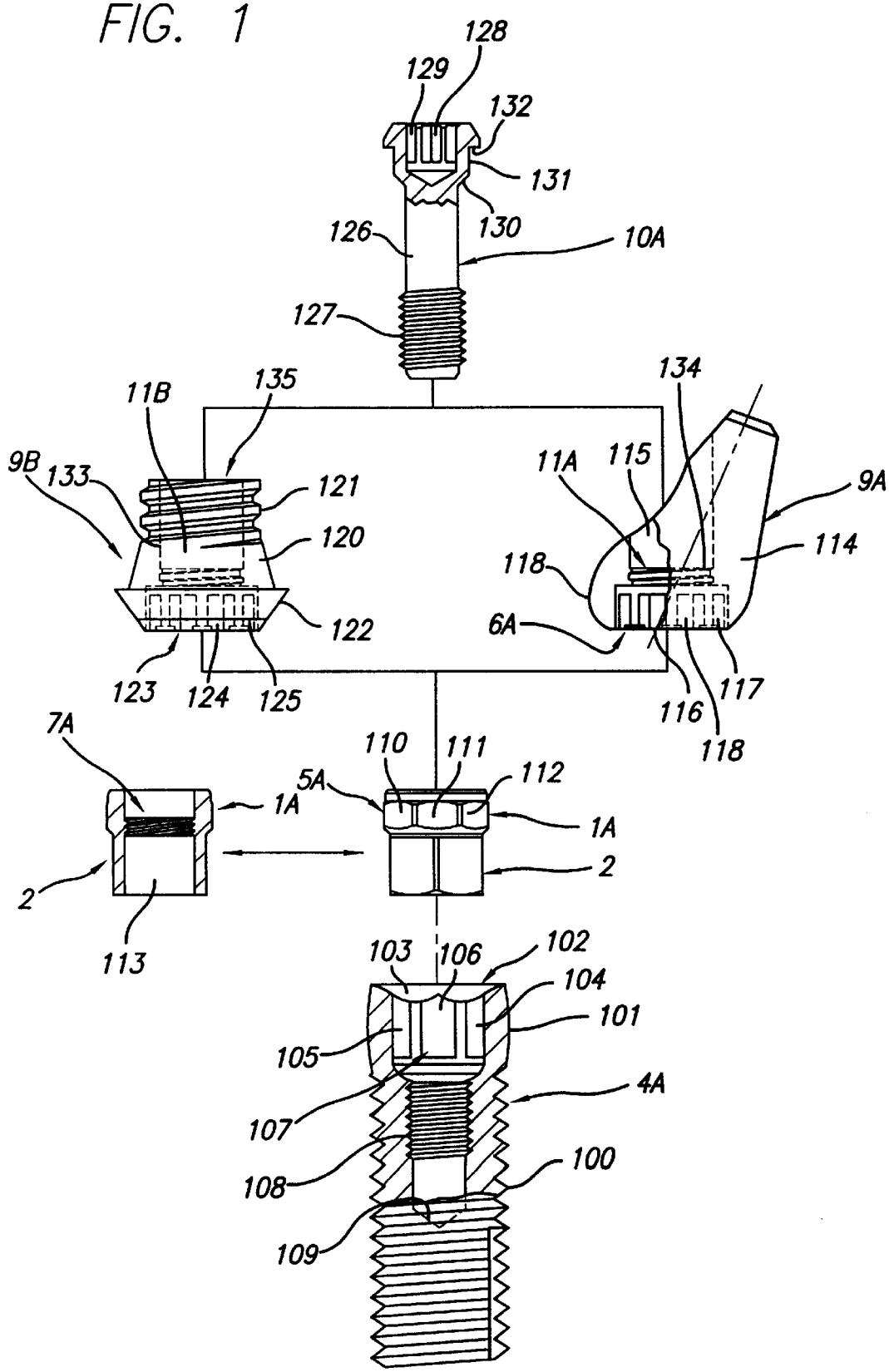
FIG. 1 shows an exploded, side elevation view, partly in cross-section, of two embodiments of the multi-part abutments of this invention for use with an endosseous dental implant having internal wrench-engaging surfaces and an internally-threaded shaft.

FIG. 1 shows endosseous dental implant 4 having external threads 100, smooth neck portion 101, internal passage 102 with chamfered surface 103 at the entrance thereto, and, below surface 103, multi-sided internal wrench-engaging surfaces 104, 105, and 106 in an internal passage 102. Internal passage 102 also includes internal threads 108. Internal passage 102 ends at conical surface 109 inside implant 4.

FIG. 1 shows two embodiments of the multi-part abutment of this invention. Both embodiments include connector 1A, also called part one. Connector 1A includes, at its proximal end, a multi-sided external wall portion 5A that includes six downwardly, outwardly tapered flats e.g. flats 110, 111, and 112, visible in FIG. 1. Connector 1A also includes, at its distal end, multi-sided surfaces 2 equal in number and length to the internal wrench-engaging surfaces 104, 105, and 106 in implant 4A. Inside connector 1A is internal passage 113 that includes internal threads 7. Threads 7 can engage a tool for disengaging connector 1A from implant 4A.

FIG. 1 also shows abutment bodies 9A and 9B. Angled abutment body 9A includes angled upper portion 114, internal, longitudinal passage 115 for receiving fastener 10, and, at its distal end, internal cavity 116 that includes a plurality of multi-sided surfaces 117, 118, among others, of a size and shape complementary to multi-sided external wall projection 5A of connector 1A. Abutment body 9A fits over external wall projection 5A on connector 1A and engages its surfaces frictionally.

Inside internal passage 115 are threads 11A. These threads 11A can engage a tool (not shown) for disengaging abutment body 9A from connector 2. Abutment body 9A also includes annular, inwardly, downwardly tapering surface 118 which seats sealingly on chamfered surface 103 when abutment body 9A is placed atop implant 4A, with or without connector 1A.

Abutment body 9B, has a downwardly, outwardly tapering side wall 120, an upper cylindrical externally threaded portion 121 and a downwardly, inwardly tapering surface 122 that seats in chamfered surface 103 of implant 4A. Internal threads 11B serve the same function as internal threads 11A in abutment body 9A. At the distal end of abutment body 9B is internal cavity 123 that includes a plurality of flats such as 124 and 125 that engage, frictionally, flats 110, 111, and 112 on connector 2.

Fastener 10 includes shank 126, with an externally threaded distal portion 127. The proximal end of fastener 10 includes internal cavity 128 with a multi-sided surface 129 to engage a suitable tool for holding, twisting or turning fastener 10. At the proximal end of fastener 10, its external surface tapers outwardly at section 130 to cylindrical section 131. The upper end of surface 131 includes flange 132 which is of sufficient diameter to engage the internal flanges 133 and 134 of abutment bodies 9B and 9A, respectively. Fastener 10 is of sufficient diameter to fit through internal passage 115 of abutment body 9A or internal passage 135 of abutment body 9B, through internal passage 113 of connector 2, and threadedly into internal threads 108 of implant 4, thus holding abutment body 9A or 9B alone, or in combination with connector 1A, to implant 4A.

Figure 3:
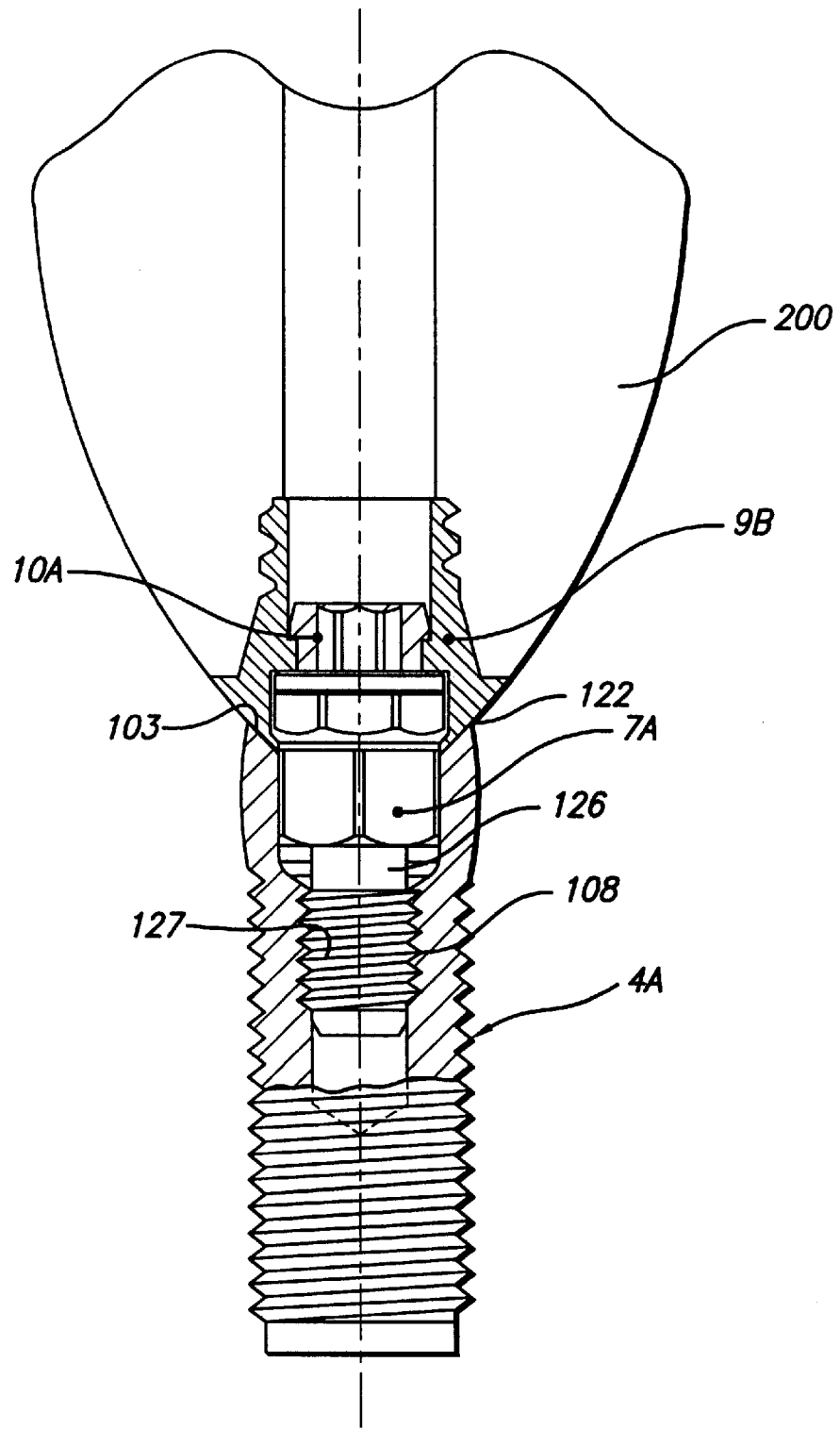
FIG. 3 shows a side elevation view, in cross-section, of the implant shown in FIG. 1 with one of the abutment embodiments shown in FIG. 1, assembled and connected to a prosthesis.

FIG. 3 shows implant 4A of FIG. 1 assembled with connector 1A and abutment body 9B. Fastener 10A passes through both connector 1A, abutment body 9B and into threaded engagement with internal threads 108 via the threaded portion 127 of shank 126, holding connector 1A and body 9B together and on implant 4. Surface 122 of abutment body 9B rests sealingly upon chamfered region 103 of implant 4A. Abutment body 9B covers connector 1A, and forms a single margin with the proximal end of implant 4A. Atop abutment body 9B is prosthesis 200, here a false tooth.

Figure 2:
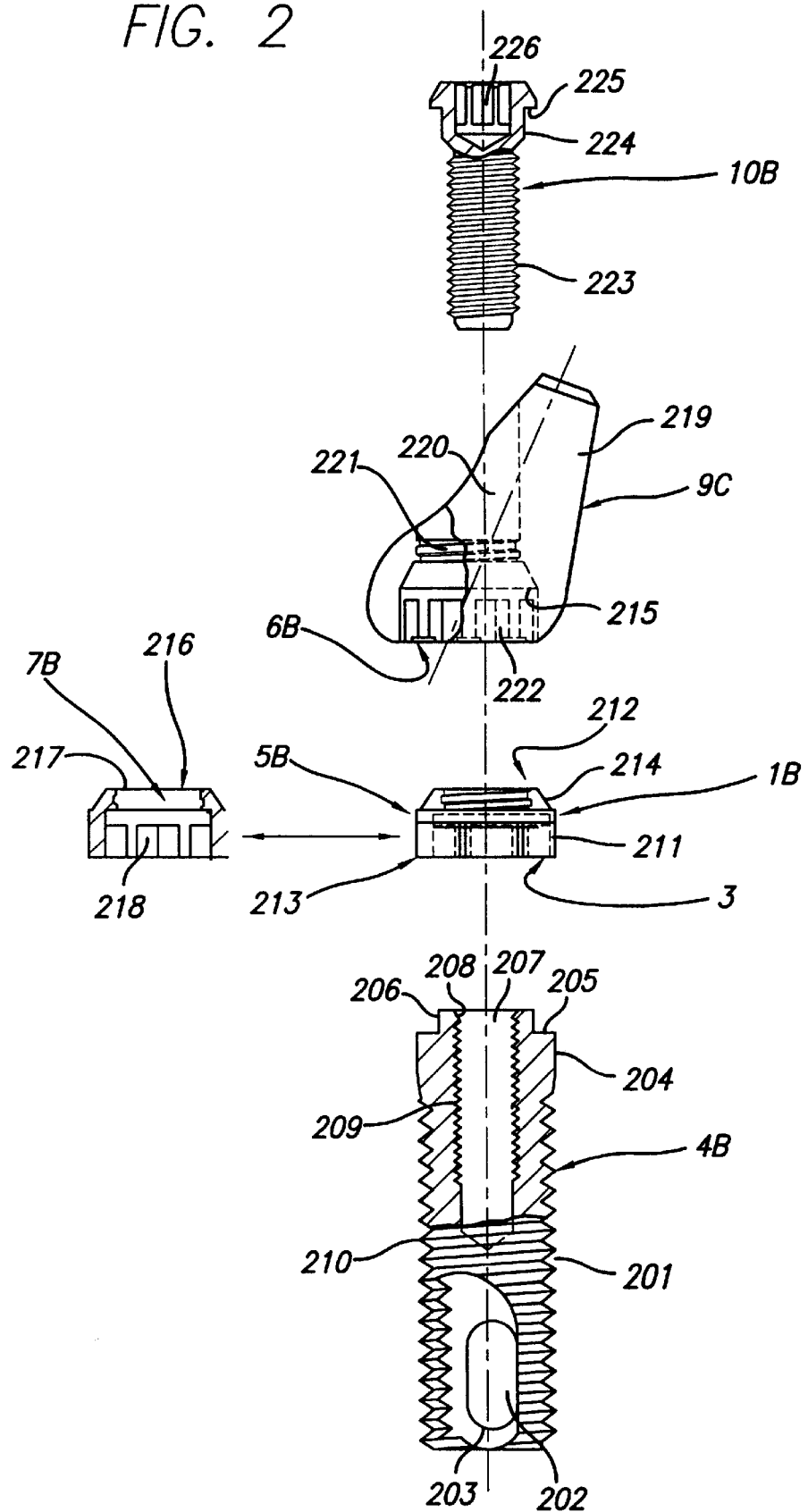
FIG. 2 shows another embodiment of the multi-part abutment of this invention in side elevation view, partly in cross-section, for use with an endosseous dental implant having an external projection for engagement with the abutment, and an internally-threaded shaft.

FIG. 2 shows endosseous dental implant 4B in an elevation cross-sectional view. Implant 4B includes externally threaded surface 201 and, at its distal end, through-hole 202 and apical hole 203. Atop externally threaded side wall 201 of implant 4B is neck portion 204. Atop neck portion 204 is flat upper surface 205 surrounding a multi-sided projection 206. Implant 4B also includes an internal passageway 207 having a chamfered region 208 at the entrance to passage 207. Inside passage 207 are internal threads 209. Passage 207 ends inside implant 4B at conical surface 210.

FIG. 2 also shows a multi-part abutment including connector 1B, abutment body 9C, and fastener 10B. Connector 1B includes external multi-sided projection 211. Each of these surfaces tapers outwardly and downwardly from the proximal end 212 of connector 1B to the distal end 213. The upper peripheral surface of connector 1B, namely surface 214, is frusto-conical in shape and complementary in size and shape to internal, frusto-conical surface 215 of abutment body 9C. Connector 1B includes internal passage 216 with internal threads 217 at the proximal end and internal multi-sided cavity 218 at the distal end.

Abutment body 9C includes angled exterior upper portion 219, internal longitudinal passage 220 with internal threads 221, and, at its distal end, internal cavity 6B with a plurality of flat surfaces 222 for seating upon and engagement with flat, external projection 211 of connector 1B.

Fastener 10B includes an externally threaded shank 223, neck portion 224, lower flange surface 225, and internal passage 226 with a multi-sided surface for engaging a suitable tool for twisting, turning or holding fastener 10B.

The abutment of FIG. 2 can be used as a multi-part abutment where connector 1B and abutment body 9C frictionally engage one another, and connector 1B is seated upon external projection 206 atop implant 4B, or as a single part abutment with abutment body 9C seated directly upon surface 205, and connector 1B omitted. Whether connector 1B is used or omitted, fastener 10B holds abutment body 9C sealingly to implant 4B when placed through internal passage 220 and into internally threaded passage 207 of implant 4B.

Because connector 1B and abutment body 9C fit together frictionally, they can be removed as a unit from implant 4B, and can also be disengaged from one another, as when abutment body 9C is cast to gold.

Figure 4:
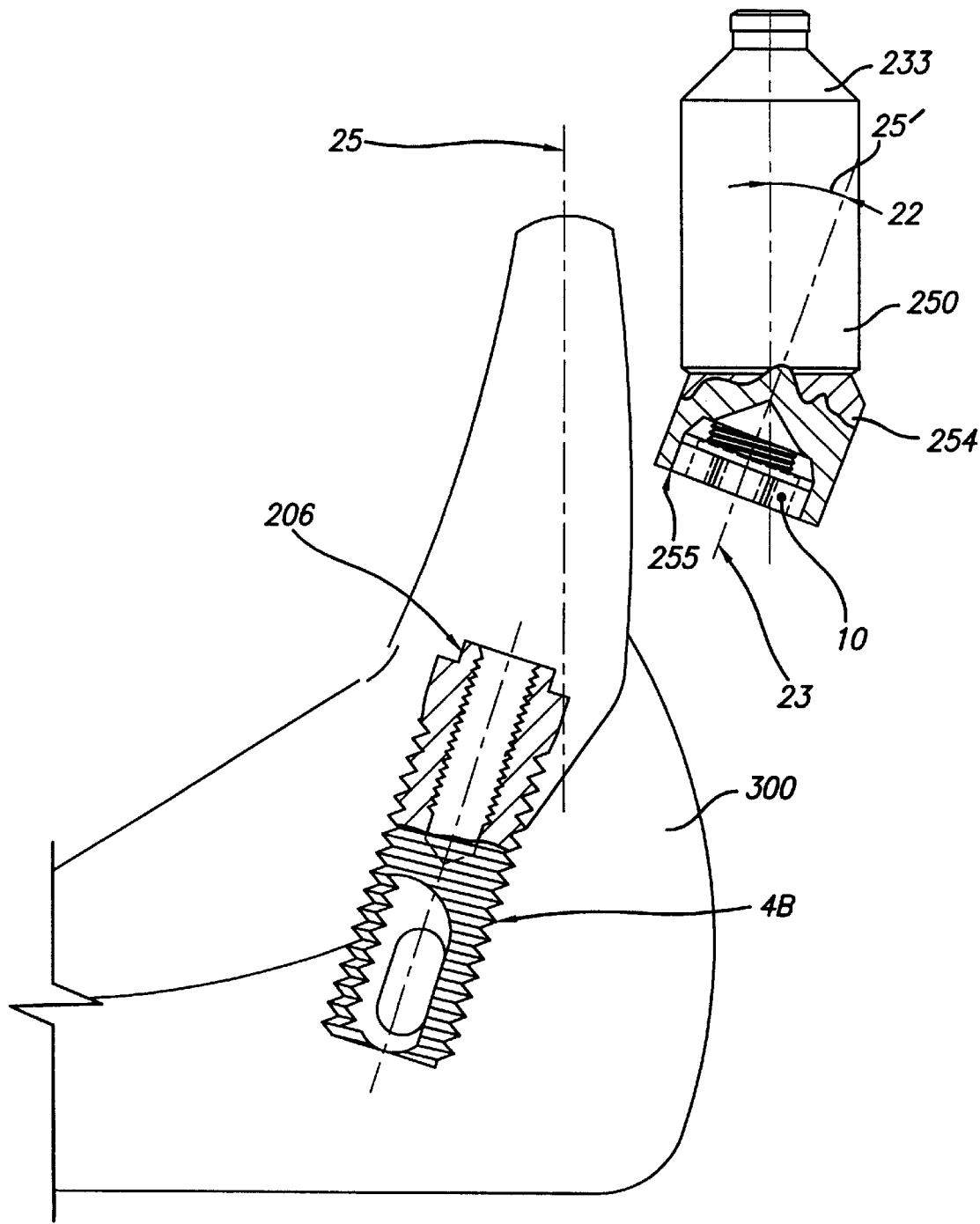
FIG. 4 shows an embodiment of the angled, one piece carrier for an abutment connector.

FIG. 4 shows implant 4B placed in jawbone tissue 300 at an angle to jawbone axis 25. Projection 206 is, therefore, also at an angle to jawbone axis 25. Carrier 250 includes cylindrical center portion 251, with an upper cylindrical portion 252 of smaller dimension than center portion 251. At its distal end, carrier 250 includes angled distal portion 254 with internal multi-sided passage 255. Passage 255 a size and shape complementary to connector 1B, and thus holds connector 1B frictionally in cavity 255. Internal multi-sided passageway 225 is oriented to angle 22 to correspond to the orientation of the body. Carrier 250 is used to place connector 1B at this desired angle upon projection 206 of implant 4B.

What is claimed is:

1. An assembly comprising a multi-part abutment comprising part one and part two and a dental implant having an opening or passage with an internal, non-circular shape at its proximal end or with an external, non-circular projection at its proximal end, said assembly comprising:

part one having a size and shape, at its distal end, removably inserted into said opening or passage, or over said external projection, and, having at its periphery, a multi-sided eternal wall portion fitted into abutment part two in a plurality of spaced positions;

part two having a size and shape sealingly engaging the proximal end of said dental implant, and having a multi-sided cavity at its distal end, that non-rotatably engages and fits over the multi-sided external wall portion of part one, said cavity having size and shape complementary to said external wall portion, sealingly engaging said periphery in a plurality of spaced positions, whereby said part two covers the top surface and said periphery of said part one and said part two sealingly engages the proximal end of said dental implant;

said part two including a proximal portion adapted to engage or form a prosthesis; and said part one and said part two including substantially colinear, internal passages that receive a single threaded fastener to join said part one and said part two to one another, and to the interior opening or passage in said dental implant.

2. The abutment of claim 1 wherein the top end portion lies at an angle with respect to the longitudinal axis of said abutment.

3. The abutment of claim 2 further comprising a single fastener of a size, shape and configuration adapted to join said part one and said part two to one another and to the interior opening or passage in said dental implant.

4. The abutment of claim 3 further comprising, at said distal end of said part one, a plurality of sides, said implant having the same number of sides as said distal end of said part one in said opening or passage.

5. The abutment of claim 2 further comprising, at said distal end of said part one, a plurality of sides, said implant having the same number of sides as said distal end of said part one in said opening or passage.

6. The abutment of claim 1 further comprising a single fastener of a size, shape and configuration adapted to join said part one and said part two to one another and to the interior opening or passage in said dental implant.

7. The abutment of claim 6 further comprising, at said distal end of said part one, a plurality of sides, said implant having the same number of sides as said distal end of said part one in said opening or passage.

8. The abutment of claim 1 further comprising, at said distal end of said part one, a plurality of sides, said implant having the same number of sides as said distal end in said of said part one opening or passage.

9. The abutment of claim 1 wherein said dental implant has an opening or passage with an internal, non-circular shape at its upper end, and wherein said part one has a size and shape, at its distal end, which fits into said opening or passage.

10. The abutment of claim 1 wherein said dental implant has an external, non-circular projection at its proximal end and wherein said part one has a size and shape, at its distal end, which fits over said external projection.

11. The combination of a carrier for a multi-part abutment and an assembly including an endosseous dental implant, said carrier having a size and shape suitable for placement of said abutment in the jawbone of a patient, said carrier including, at its distal end, an internal multi-sided cavity to engage a connector, and to hold said connector at an angle to the longitudinal axis of said carrier, whereby proper placement of said connector in the jawbone of a patient is feasible, said assembly comprising: a multi-part abutment comprising part one and part two and a dental implant having an opening or passage with an internal, non-circular shape at its proximal end or with an external, non-circular projection at its proximal end, said assembly comprising:

part one having a size and shape, at its distal end, removably inserted into said opening or passage, or over said external projection, and, having at its periphery, a multi-sided external wall portion fitted into abutment part two in a plurality of spaced positions;

part two having a size and shape sealingly engaging the proximal end of said dental implant, and having a multi-sided cavity at its distal end, that non-rotatably engages and fits over the multi-sided external wall portion of part one, said cavity having size and shape complementary to said external wall portion, sealingly engaging said periphery in a plurality of spaced positions, whereby said part two covers the top surface and said periphery of said part one and said part two sealingly engages the proximal end of said dental implant;

said part two including a proximal portion adapted to engage or form a prosthesis; and said part one and said part two including substantially colinear, internal passages that receive a single threaded fastener to join said part one and said part two to one another, and to the interior opening or passage in said dental implant.

* * * * *